United States Patent [19]
Engh et al.

[11] Patent Number: 6,150,410
[45] Date of Patent: Nov. 21, 2000

[54] PH INDEPENDENT EXTENDED RELEASE PHARMACEUTICAL FORMULATION

[75] Inventors: Kevin R. Engh, Mundelein; Yihong Qiu, Gurnee, both of Ill.; Venkatramana M. Rao, Lawrence, Kans.

[73] Assignee: Abbott Laboratories, Abbott Park, Ill.

[21] Appl. No.: 09/490,531

[22] Filed: Jan. 25, 2000

Related U.S. Application Data

[60] Provisional application No. 60/118,701, Feb. 4, 1999.

[51] Int. Cl.⁷ .......................... A61K 31/19; A61K 47/30; A61K 47/00
[52] U.S. Cl. .................. 514/557; 514/772.3; 514/781
[58] Field of Search ............................... 514/557, 772.3, 514/781

[56] References Cited

U.S. PATENT DOCUMENTS

| | | |
|---|---|---|
| 4,369,172 | 1/1983 | Schor et al. . |
| 4,913,906 | 4/1990 | Friedman et al. . |
| 4,988,731 | 1/1991 | Meade . |
| 5,009,897 | 4/1991 | Brinker et al. . |
| 5,017,613 | 5/1991 | Aubert et al. . |
| 5,019,398 | 5/1991 | Daste . |
| 5,055,306 | 10/1991 | Barry et al. . |
| 5,169,642 | 12/1992 | Brinker et al. . |
| 5,185,159 | 2/1993 | Aubert et al. . |
| 5,212,326 | 5/1993 | Meade . |
| 5,486,365 | 1/1996 | Takado et al. . |
| 5,589,191 | 12/1996 | Ukigaya et al. . |

FOREIGN PATENT DOCUMENTS

| | | |
|---|---|---|
| 0334167 | 9/1989 | European Pat. Off. . |
| 9427587 | 8/1994 | WIPO . |
| 9706787 | 2/1997 | WIPO . |

OTHER PUBLICATIONS

Bialer, et al., "Metabolism of Antiepileptic Drugs", pp. 143–151, R.H. Levy, Ed. Raven Press, NY (1984).
Int. J. Pharmaceutics, 20: 53–63 (1984).
Biopharmaceutics and Drug Disposition, 6: 401–411 (1985).
Israel J. Med. Sci., 20: 46–49 (1995).
Remington's Pharmaceutical Sciences, 18$^{th}$ Ed., p. 1677, Mack Pub. Co., Easton, PA (1990).
Dressman, et al., Pharm Res., 15: 1 (1998).

*Primary Examiner*—Raymond Henley, III
*Attorney, Agent, or Firm*—Dugal S. Sickert

[57] ABSTRACT

Pharmaceutical formulations of acidic pharmacologic agents which demonstrate improved uniformity of release over the wide range of pH values encountered between the stomach and intestinal tract comprise an acidic pharmacologic agent dissolved or dispersed in a matrix comprising about 10 weight percent to about 40 weight percent of a a neutral water-swellable hydrophilic polymer and 20 weight percent to about 50 weight percent of an acid-soluble polymer which swells in water at pH values above about 5. A particularly preferred formulation comprises divalproex sodium. Also disclosed are pre-tablet granulations and process for preparing both the pre-tablet granulation and the tablet unit dosage form.

30 Claims, 6 Drawing Sheets

PH INDEPENDENT EXTENDED RELEASE PHARMACEUTICAL FORMULATION

REFERENCE TO RELATED APPLICATION

This application is a conversion of U.S. Provisional Patent Application 60/118,701, filed on Feb. 4, 1999.

TECHNICAL FIELD

This invention relates to pharmaceutical formulations. More particularly, the present invention concerns extended release pharmaceutical formulations containing an acidic pharmacologic agent which formulations have reduced dependence of release rate on pH.

BACKGROUND OF THE INVENTION

The normal pH of gastric juices is about pH 1, while the pH in the intestinal tract averages about pH 7. This fact has been used to advantage for years in so-called "enteric coated" pharmaceutical formulations. These formulations are generally in the form of tablets coated with a substance which is insoluble or sparingly soluble in acidic solutions, but which dissolves rapidly at higher pH. Such enteric coated formulations permit the oral administration of drugs which would present problems if released in the stomach, such as irritation of the stomach lining. Moreover, enteric-coated tablets also permit extending the release of a drug over time. For example, a tablet can be formulated by compressing granules containing the drug, some of which granules are enteric coated and some of which are not. As the tablet disintegrates, the non-enteric coated granules dissolve in the stomach, immediately releasing the drug, while the enteric coated granules pass to the intestine before dissolving to release the drug. In this way, release of the drug can be extended over the time the drug is resident in both the stomach and intestine. Such an extended release system is crude, essentially releasing the drug in a bi-modal manner. It is generally desirable to release a drug more smoothly over time than can be done by a partially enteric coated formulation of the type just described.

In the effort to achieve smooth, controllable release of acidic pharmacologic agents, several systems have been devised. These fall into one of three general classes: osmotic systems, dissolution systems, and diffusion systems. An example of an osmotic system is a tablet consisting of a core of drug surrounded by a semi-permeable membrane containing a small orifice. When the tablet is exposed to an aqueous body fluid, water flows into the tablet through the semi-permeable membrane due to the osmotic pressure difference. The drug is then pumped out of the tablet through the orifice at a constant rate controlled by the parameters of drug concentration, orifice diameter, osmotic pressure difference, etc., until the drug concentration inside the tablet falls below saturation.

Dissolution systems take advantage of the inherent dissolution rate of the drug itself, or of a particular salt or derivative. Alternatively, the drug can be coated with a slowly dissolving coating, or by incorporating the drug into a slowly dissolving carrier.

Diffusion systems include both reservoir devices, in which a core of drug is surrounded by a polymeric membrane, and matrix devices in which dissolved or dispersed drug is distributed uniformly throughout an inert polymer matrix. The release of drug from a reservoir system involves the flow of drug through the membrane, and is controlled by Fick's first law of diffusion. Depending upon the shape of the tablet, the equation describing the release will vary.

In matrix systems, the mechanism of drug release is assumed to involve dissolution of the drug from the surface layer of the device first, followed by dissolution from the underlying layer and diffusion through the overlying drug-depleted layer, etc.

The design of a sustained or extended release formulation for drugs which are acidic present particular problems for the pharmaceutical formulator. The solubility of such drugs in gastric juices is typically low as a result of the repression of ionization of the acid by the low pH in the stomach. On the other hand, such acidic drugs dissolve rapidly in the intestine, sometimes more rapidly than desired. The various systems described above lend themselves readily to the formulation of extended release formulations of drugs which are unaffected by pH as they traverse the alimentary canal, but do not provide adequate formulations where the drug has widely varying pH-dependent release rates between the stomach and intestinal tract.

One such acidic pharmacologic agent is 2-propylpentanoic acid, more commonly known as valproic acid (VPA), which is effective in the treatment of epileptic seizures or as an antipsychotic agent. U.S. Pat. No. 4,988,731 to Meade discloses an oligomer having a 1:1 molar ratio of sodium valproate and valproic acid containing 4 units, and U.S. Pat. No. 5,212,326 to Meade discloses a stable, non-hygroscopic solid form of valproic acid which comprises an oligomer having 1:1 molar ratio of sodium valproate and valproic acid and containing four to six units. Divalproex sodium (sodium hydrogen divalproate), a comple formed between one mole of 2-propylpentanoic acid and its sodium salt, is one of the most widely accepted antiepileptic agents currently available.

However, despite its efficacy in the treatment of epilepsy, valproic acid is poorly soluble in the stomach and has also been shown to exhibit an elimination half-life which is shorter than other commonly used anti-epileptic agents. Half-lives for the drug of between six and seventeen hours in adults and between four and fourteen hours in children have been reported. This leads to substantial fluctuations in the plasma concentration of the drug, especially in chronic administration. To maintain reasonable stable plasma concentrations, it is necessary to resort to frequent dosing, and the resulting inconvenience to the patient often results in lowered compliance with the prescribed dosing regimen. Moreover, widely fluctuating plasma concentrations of the drug may result in administration of less than therapeutic amounts of the drug in a conservative dosing regimen, or to amounts too large for the particular patient in an aggressive dosing regimen.

To overcome these disadvantages, a concerted effort has been devoted to the discovery of formulations which will maintain more constant plasma levels of acidic drugs in general, and valproic acid in particular, following administration. The ultimate goal of these studies has been the discovery of a formulation which affords stable plasma levels in a once-a-day dosing regimens for such drugs. These efforts fall generally into one of two categories: (a) finding a form of the active ingredient which is more uniformly released to the body metabolically, and (b) finding a formulation which delivers the drug by either a timed- or controlled-release mechanism.

With regard to valproic acid, U.S. Pat. No. 4,369,172 to Schor, et al. describes, for example, a prolonged release therapeutic composition based on mixtures of hydroxypropylmethyl cellulose, ethyl cellulose and/or sodium carboxymethyl cellulose. The patentees provide a long list of therapeutic agents which they suggest can be incorporated into the formulation including sodium valproate.

U.S. Pat. No. 4,913,906 to Friedman, et al. discloses a controlled release dosage form of valproic acid, its amide, or one of its salts or esters in combination with a natural or synthetic polymer, pressed into a tablet under high pressure.

U.S. Pat. No. 5,009,897 to Brinker, et al. discloses granules, suitable for pressing into tablets, the granules comprising a core of divalproex sodium and a coating of a mixture of a polymer and microcrystalline cellulose.

U.S. Pat. No. 5,019,398 to Daste discloses a sustained-release tablet of divalproex sodium in a matrix of hydroxypropylmethyl cellulose and hydrated silica.

U.S. Pat. No. 5,055,306 to Barry, et al. discloses an effervescent or water-dispersible granular sustained release formulation suitable for use with a variety of therapeutic agents. The granules comprise a core comprising the active ingredient and at least one excipient, and a water insoluble, water-swellable coating comprising a copolymer of ethyl acrylate and methyl methacrylate and a water soluble hydroxylated cellulose derivative. The patentees suggest a list of therapeutic agents which may be used in the formulation of the invention, including sodium valproate.

U.S. Pat. No. 5,169,642 to Brinker, et al. disclose a sustained release dosage form comprising granules of divalproex sodium or amides or esters of valproic acid coated with a sustained release composition comprising ethyl cellulose or a methacrylic methyl ester, a plasticizer, a detackifying agent, and a slow-release polymeric viscosity agent.

U.S. Pat. No. 5,185,159 to Aubert, et al. disclose a formulation of valproic acid and sodium valproate which is prepared without the use of either a binder or a granulating solvent. The formulation optionally contains precipitated silica as an anti-sticking or detackifying agent.

U.S. Pat. No. 5,589,191 to Exigua, et al. discloses a slow release sodium valproate tablet formulation in which the tablets are coated with ethyl cellulose containing silicic acid anhydride.

Published PCT application WO 94/27587 to Ayer, et al. discloses a method for control of epilepsy by delivering a therapeutic composition of valproic acid or a derivative in combination with a polyalkylene oxide.

Bailer, et al., "Metabolism of Antiepileptic Drugs," pp. 143–151, R. H. Levy, Ed., Raven Press, New York, 1984; *Int. J. Pharmaceutics*, 20: 53–63 (1984); and *Biopharmaceutics and Drug Disposition*, 6: 401–411 (1985); and *Israel J. Med. Sci.*, 20: 46–49 (1995) report the pharmacokinetic evaluation of several sustained release formulations of valproic acid.

Despite these efforts, however, there remains a need for formulations of acidic pharmacologic agents (in general), and valproic acid (in particular) which demonstrate less dependence in dissolution and release rate upon variation in pH in the alimentary canal.

SUMMARY OF THE INVENTION

In accordance with the present invention, extended release pharmaceutical formulations of acidic pharmacologic agents having diminished dependence of release rate upon pH and gastric residence time (GRT) comprise a therapeutically effective amount of the acidic pharmacologic agent dissolved or dispersed in a polymer matrix comprising (a) from about 10 weight percent to about 40 weight percent of a pharmaceutically acceptable neutral, water-swellable, hydrophilic polymer, and (b) from about 20 weight percent to about 50 weight percent of a pharmaceutically acceptable acid soluble polymer which is water swellable above about pH 5, all percentages by weight based upon the total weight of the formulation.

The formulations provide for enhanced release rate of the acidic pharmacologic agent in the stomach where the pH of gastric juices is low, and diminished release rate of the acidic pharmacologic agent at neutral or slightly alkaline pH in the intestinal tract. The result is more uniform release of the pharmacologic agent as the agent moves from the acidic environment of the stomach to the neutral or slightly alkaline environment of the upper and lower intestinal tracts. In addition, the release of the agent has less dependency upon the time the agent is resident in the acidic environment of the stomach.

In an alternative embodiment, the present invention comprises a pharmaceutical formulation comprising a therapeutically effective amount of divalproex sodium dissolved or dispersed in a matrix comprising from about 10 weight percent to about 40 weight percent of a neutral, water swellable hydrophilic polymer and from about 20 weight percent to about 50 weight percent of an acid soluble polymer which is water swellable at pH values above about 5, all weight percentages based upon the total weight of the granular composition.

In another embodiment, the present invention provides a dry granular composition suitable for compressing into a tablet dosage form, the granular composition comprising particles containing an acidic pharmacologic agent dissolved or dispersed in a matrix comprising from about 10 weight percent to about 40 weight percent of a neutral, water swellable hydrophilic polymer and from about 20 weight percent to about 50 weight percent of an acid soluble polymer which is water swellable at pH values above about 5, all weight percentages based upon the total weight of the granular composition.

In a further embodiment, the present invention provides a process for preparing a granular pharmaceutical composition suitable for pressing into tablets comprising the steps of (a) dry blending a mixture of from about 5 weight percent to about 50 weight percent of an acidic pharmacologic agent, from about 20 weight percent to about 40 weight percent of a neutral, water-swellable hydrophilic polymer, from about 20 weight percent to about 50 weight percent of an acid soluble polymer which is water-swellable at pH values above about 5 to form a uniform mixture; (b) wet granulating the dry uniform mixture from step (a); and (c) drying and sizing the wet granules from step (b), wherein all percentages are based upon to total weight of the granulation.

In yet another embodiment, the present invention provides a method of preparing a controlled release tablet dosage form of an acidic pharmacologic agent comprising the steps of (a) dry blending a mixture of from about 5 weight percent to about 50 weight percent of an acidic pharmacologic agent, from about 20 weight percent to about 40 weight percent of a neutral, water-swellable hydrophilic polymer, from about 20 weight percent to about 50 weight percent of an acid soluble polymer which is water-swellable at pH values above about 5 to form a uniform mixture; (b) wet granulating the dry uniform mixture from step (a); (c) drying and sizing the wet granules from step (b); and (d) compressing the blended granules of step (c) under a force ranging between about 2000 lbf (about $8.9 \times 10^3$ Newtons) and about 10,000 lbf (about $4.45 \times 10^4$ Newtons).

DETAILED DESCRIPTION OF THE PREFERRED EMBODIMENTS

As used throughout this specification and the appended claims, the terms "sustained or extended release", "prolonged release", and "controlled release", as applied to drug formulations, have the meanings ascribed to them in "Remington's Pharmaceutical Sciences," $18^{th}$ Ed., p.1677, Mack Pub. Co., Easton, Pa. (1990). Sustained or extended release drug systems include any drug delivery system which achieves the slow release of drug over an extended period of time, and include both prolonged and controlled release systems. If such a sustained release system is effective in maintaining substantially constant drug levels in the blood or target tissue, it is considered a controlled release drug delivery system. If, however, a drug delivery system is unsuccessful at achieving substantially constant blood or tissue drug levels, but nevertheless extends the duration of action of a drug over that achieved by conventional delivery, it is considered a prolonged release system.

The formulations of the present invention provide an extended or prolonged release formulation for acidic pharmacologic agents. By the term "acidic pharmacologic agent" is meant any compound having therapeutic activity and exhibiting a pKa value less than about 6.0. While not holding to one theory to the exclusion of others, it is believed that the formulations of the present invention normalize or regularize the release rate of acidic pharmacologic agents over a wide range of pH values by the interaction of the effects on release of the two polymer components of the matrix in which the pharmacologic agent is dissolved or dispersed. At low pH values in the stomach, the acid soluble polymer is believed to have the greatest effect on release of the pharmacologic agent. In this environment, where the pharmacologic agent is typically of low solubility, the acid-soluble or ionizable polymer is protonated and begins dissolving out of the formulation matrix. This aids in the release of the pharmacologic agent in the regions of the matrix where the agent is dissolved or dispersed in this component of the polymer matrix in either or both of two ways. First, the dissolution of the acid-soluble polymer component of the matrix physically aids the release of the pharmacologic agent, and second, protonation of the acid-soluble polymer by the acidic gastric juices raises the pH in the local environment of the formulation matrix to levels where the acidic pharmacologic agent is more soluble.

At the neutral or alkaline pH values encountered in the intestine, the acid-soluble polymer swells, along with the neutral water-swellable second component of the formulation polymer matrix, thus presenting a more tortuous route through which the acidic pharmacologic agent must migrate to be released from the formulation matrix. In this manner, the release rate of the pharmacologic agent is both accelerated at low pH and diminished at higher pH to provide a more uniform or regularized release rate over a wide pH range.

Moreover, since the release of the acidic pharmacologic agent in the acidic environment of the stomach and the neutral or alkaline pH of the intestine is moderated by the polymer matrix of the formulation, the overall release of the pharmacologic agent is less dependent upon the time the agent is resident in the stomach.

TABLE 1

Typical Gastric Residence Times (GRT) of Pharmaceutical Dosage Sizes

| Dosage Size | State  | GRT (min.) |
|-------------|--------|------------|
| 1 mm        | Fasted | 60–150     |
| 3 mm        | Fasted | 15–240     |
| 14 mm       | Fasted | 15–210     |
| 1 mm        | Fed    | 101 ± 53   |
| 3.2 mm      | Fed    | 152 ± 40   |
| 9 mm        | Fed    | 105 > 600  |
| 14 mm       | Fed    | 180 > 780  |

Table 1, reproduced from Dressman, et al., *Pharm, Res.*, 15:1 (1998) shows the gastric residence time (GRT) of drug formulations of various dosage size in patients in both the fed and fasting states.

In a preferred embodiment, the invention provides an oral dosage form of valproic acid having diminished dependence of the release rate on pH. The term "valproic acid" is meant to encompass the compound 2-propylpentanoic acid per se, and salts thereof including the complex formed between one mole of 2-propylpentanoic acid and its sodium salt, commonly referred to as divalproex sodium. Divalproex sodium is disclosed in U.S. Pat. Nos. 4,988,731 and 5,212,326 to Meade and can be represented by the following formula where m ranges from two to about six:

Divalproex sodium is a typical acidic pharmacologic agent, having a pKa of 4.8 and, as shown in Table 2, has a wide-ranging solubility over the pH range between pH 1.0 and pH 6.7, that is, over the range of pH difference between the stomach and the intestinal tract. It is therefore a good example of an acidic pharmacologic agent for illustrating the formulations of the present invention.

TABLE 2

Solubility of Divalproex Sodium at Various Values of pH

| pH | Solubility (mg/mL) |
|---|---|
| 1.0 | 1.0 |
| 4.7 | 2.0 |
| 4.84 | 3.4 |
| 5.87 | 21.0 |
| 6.17 | 36.0 |
| 6.7 | 200 |

In arriving at the resent invention, various systems were contemplated to obtain a formulation which would enhance the solubility/release of an acidic pharmacologic agent at low pH and retard its release at higher pH. In this manner, the release of the agent would be more regularized as it passed from the stomach into the intestinal tract. Divalproex sodium was selected as a representative example of an acid pharmacologic agent.

One approach involved embedding the drug in a polymer matrix along with an basic (alkaline) excipient which had the desired compressibility for tabletting, which was compatible with the other ingredients of the formulation, and which would enhance the solubility/release in the acidic environment of the stomach by raising the pH in the local environment of the matrix and by rapid leaching. In this manner, it was expected that the acidic drug would be released more quickly by the enhanced solubility/release of the excipient than from a similar polymer matrix lacking such an excipient. On the other hand, it was expected that the normally rapid dissolution/release of the acidic pharmacologic agent at the higher pH values encountered in the intestinal tract would be slowed somewhat by the need for the drug to diffuse through the polymer matrix and through the remaining undissolved excipient in the formulation which becomes insoluble in the intestine.

Using this approach, two formulations were tested. In a first formulation (Formulation 3 below), an anhydrous dibasic calcium phosphate which is soluble in acidic pH, but insoluble at neutral pH, and has superior compressibility and disintegration, was mixed, together with the drug, hydroxypropylmethyl cellulose (Methocel® grade K4MP CR, Dow Chemical), and lactose, and pressed into tablets. The anhydrous dibasic calcium phosphate used is described in U.S. Pat. No. 5,486,365 and is available as Fujicalin® from Fuji Chemical Industries, Inc.

In a second formulation (Formulation 4 below), a finely powdered amorphous magnesium aluminosilicate, also being basic and having superior compressibility and dispersion, was substituted for the dibasic calcium phosphate. This material is available as Neusilin®, also from Fuji Chemical Industries, Inc. For comparative purposes, an extended release formulation (Formulation 2) of divalproex sodium based upon a polymer matrix system, but lacking either of the two excipients described above was used as a comparative control.

As shown by the data compiled in the accompanying drawing figures, neither the approach utilized in Formulation 3 nor Formulation 4 resulted in the desired regularization of drug release over a wide range of pH, nor did the typical matrix formulation comprising a neutral water-swellable polymer as in Formulation 2. Only the preferred formulation of the invention (Formulation 1), which comprised a matrix of a neutral water-swellable polymer, and a polymer which was both acid-soluble and water swellable at higher pH produced the desired results.

Figure 1:
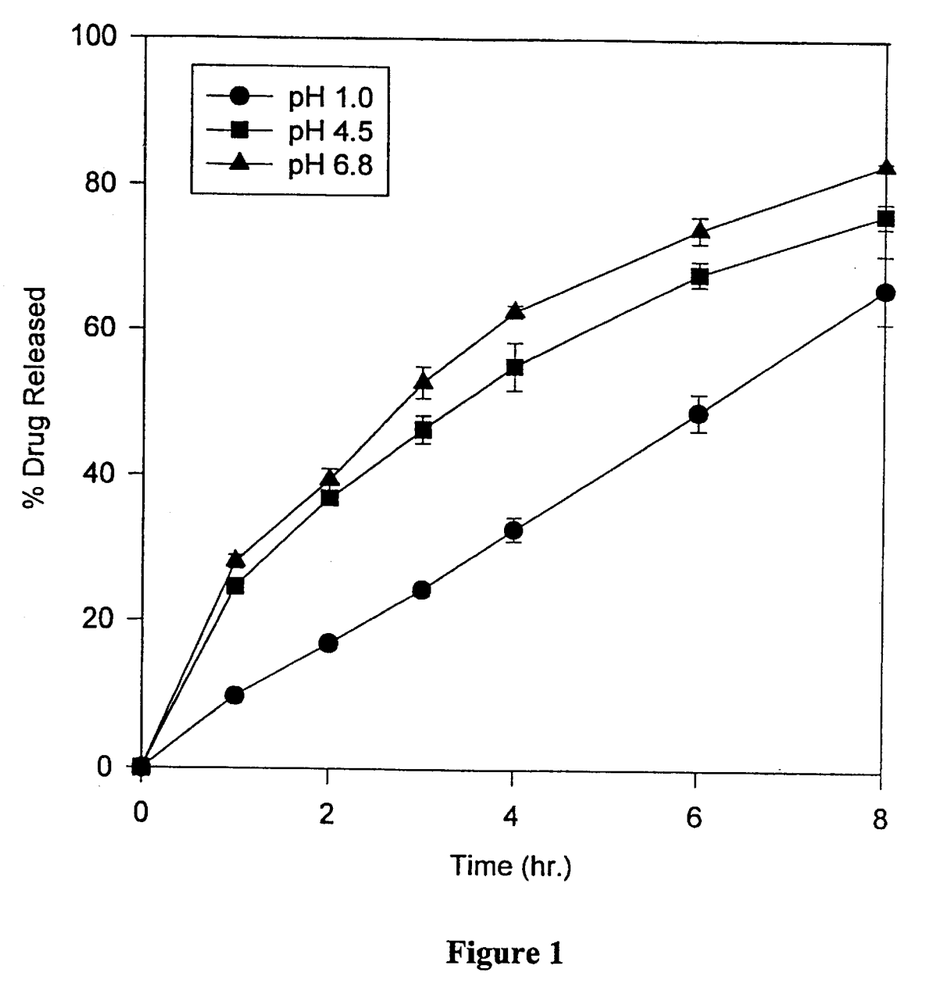
FIG. 1 is a graphical representation of data showing the percent release over time of drug at various values of pH from a control pharmaceutical formulation comprising a polymer matrix extended release formulation, but lacking any ingredient intended to moderate the pH effect.

FIG. 1 shows the percent release of drug over time from the control formulation (Formulation 2). Formulation 2 was a matrix extended release formulation of the active drug, but lacking any ingredient intended to moderate the pH effect. Three curves are shown, depicting the release of the drug at pH 1.0, pH 4.5 and pH 6.8. The graph clearly shows slower release of the drug at pH 1.0 than at the higher pH values as would be expected of an acidic pharmacologic agent. Moreover there is an undesirable range, after eight hours, in the total of released drug.

Figure 2:
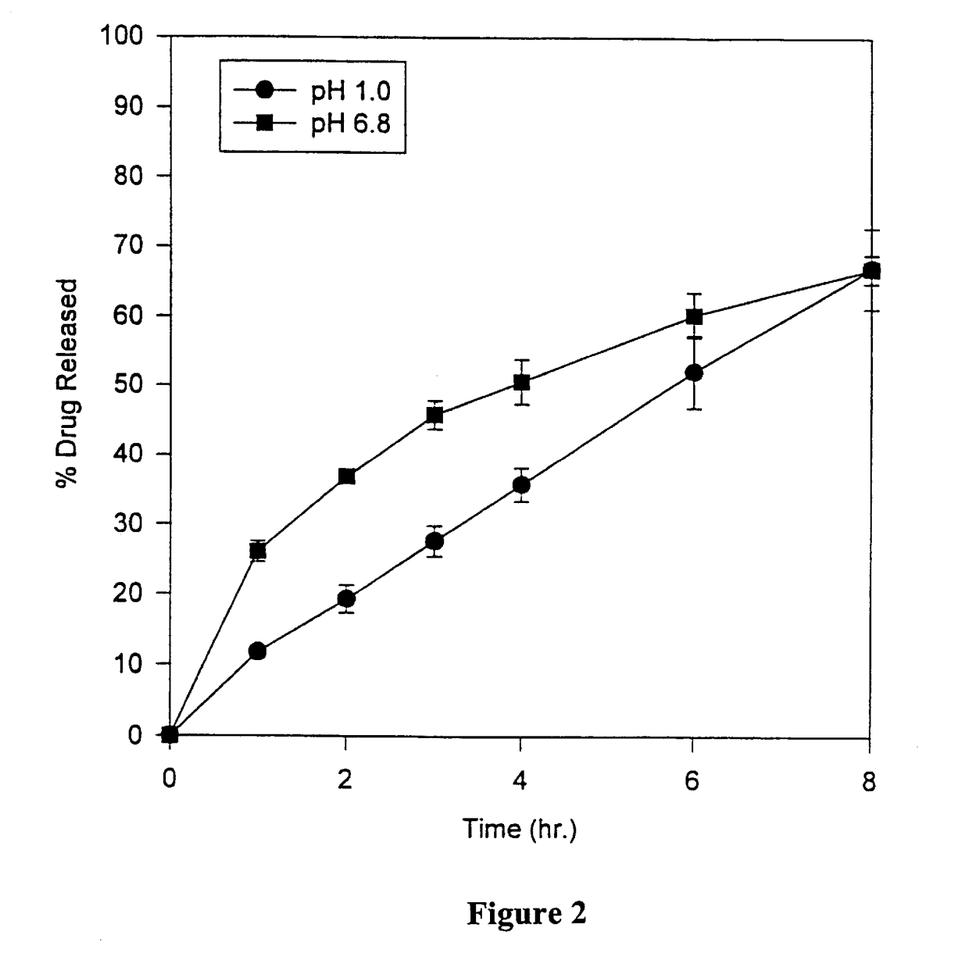
FIG. 2 is a graphical representation of data showing the percent release over time of drug at various values of pH from a formulation comprising a polymer matrix extended release formulation, and further containing anhydrous dibasic calcium phosphate.

FIG. 2 depicts the percent release over time of drug from the formulation containing anhydrous dibasic calcium phosphate (Formulation 3) at pH 1.0 and pH 6.8. In this instance, the total drug released after eight hours is the same at both pH values, but there is still a difference before that point in release rate of the drug at the different pH values.

Figure 3:
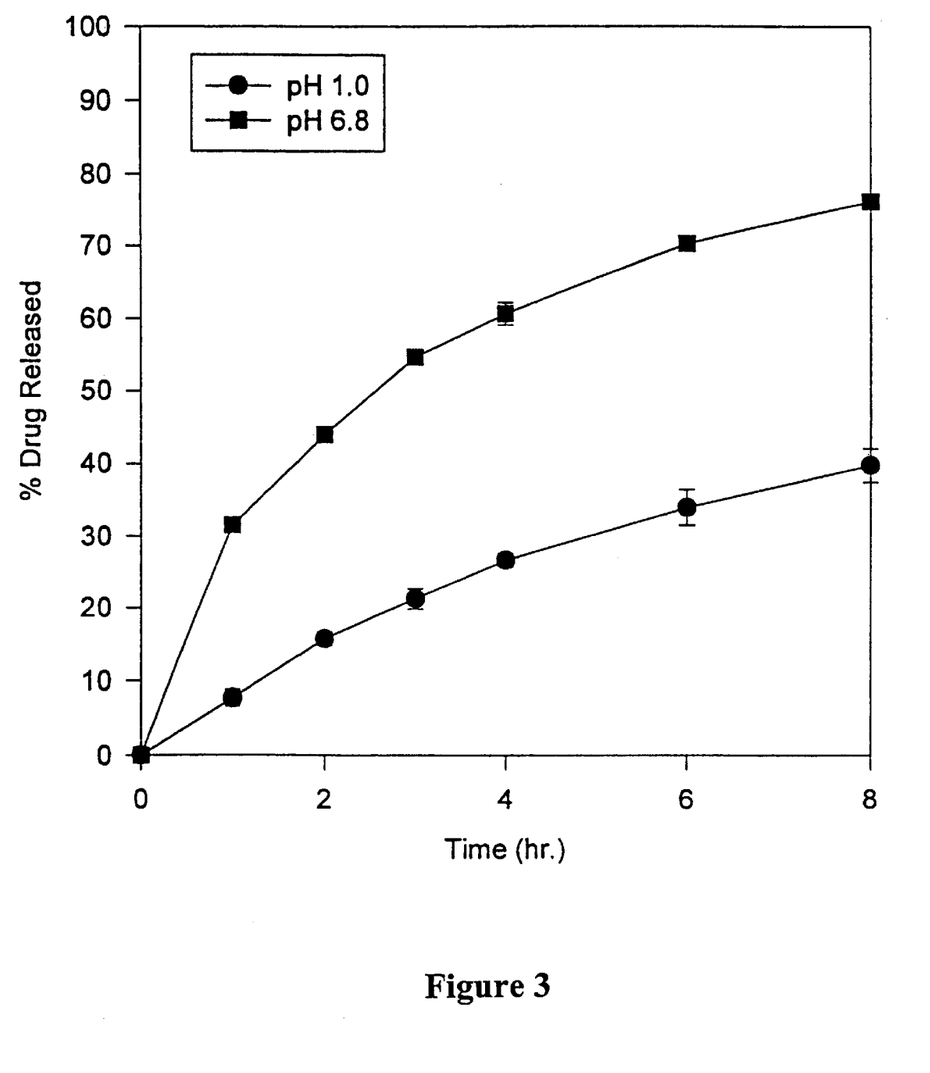
FIG. 3 is a graphical representation of data showing the percent release over time of drug at various values of pH from a formulation comprising a polymer matrix extended release formulation, and further containing amorphous magnesium aluminometasilicate.

FIG. 3 shows the percent release over time of drug from the formulation containing amorphous magnesium aluminometasilicate (Formulation 4) at pH 1.0 and pH 6.8. The result is clearly unacceptable as a solution to the problem of alleviating pH dependency upon drug release rate. The rates at the two values of pH vary widely, and the total amount of drug released at the lower pH after eight hours is unacceptably low.

Figure 4:
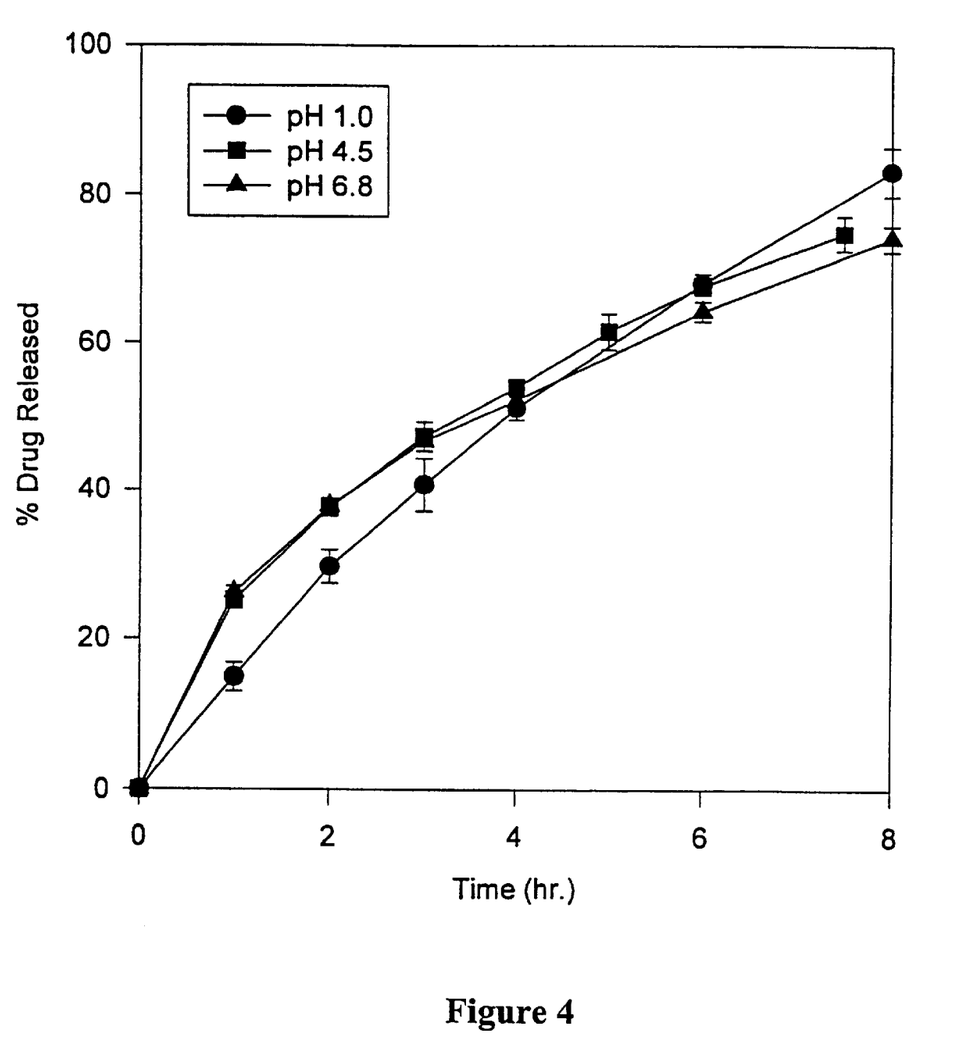
FIG. 4 is a graphical representation of data showing the release rate over time of drug at various values of pH for the preferred formulation of the present invention.

FIG. 4 depicts the percent release over time of drug from the preferred formulation of the present invention (Formulation 1) at pH 1.0, 4.5 and 6.8. As can be seen by the figure, the three curves depicting percent release of the drug track one another comparatively closely.

The dependence of release of valproic acid on gastric residence time from two formulations was also tested. One formulation was a typical prior art formulation in which the drug was dispersed in a hydroxypropyl methylcellulose matrix, and the other was a formulation according to the present invention in which the drug was in a matrix comprising a mixture of a neutral hydroxypropyl methylcellulose polymer and an acid-soluble dimethylaminoethyl-modified methacrylate polymer. The drug formulations were exposed to 0.1 M HCl solution in vitro to simulate gastric conditions and in pH 6.8 buffer (tribasic phosphate) to simulate intestinal conditions in a USP Apparatus II stirring apparatus, and the amount of drug released measured by fluorescent polarization immunoassay as described below. Zero hours gastric residence time data represent data from experiments in which the release rate from the formulations were followed from the beginning in tribasic phosphate buffer at pH 6.8. Two- and four-hour gastric residence time data are data from experiments in which the drug formulations were initially exposed for 2 or 4 hours, respectively to 0.1 M HCl and, for the remainder of the experiments to pH 6.8 tribasic buffer. The latter experiments thus simulate exposure of the drug to the acidic environment of the stomach for a pre-determined period, followed by exposure to the neutral or slightly alkaline intestinal environment for the remaining time of the experiment. The results are depicted in FIGS. 5 and 6.

Figure 5:
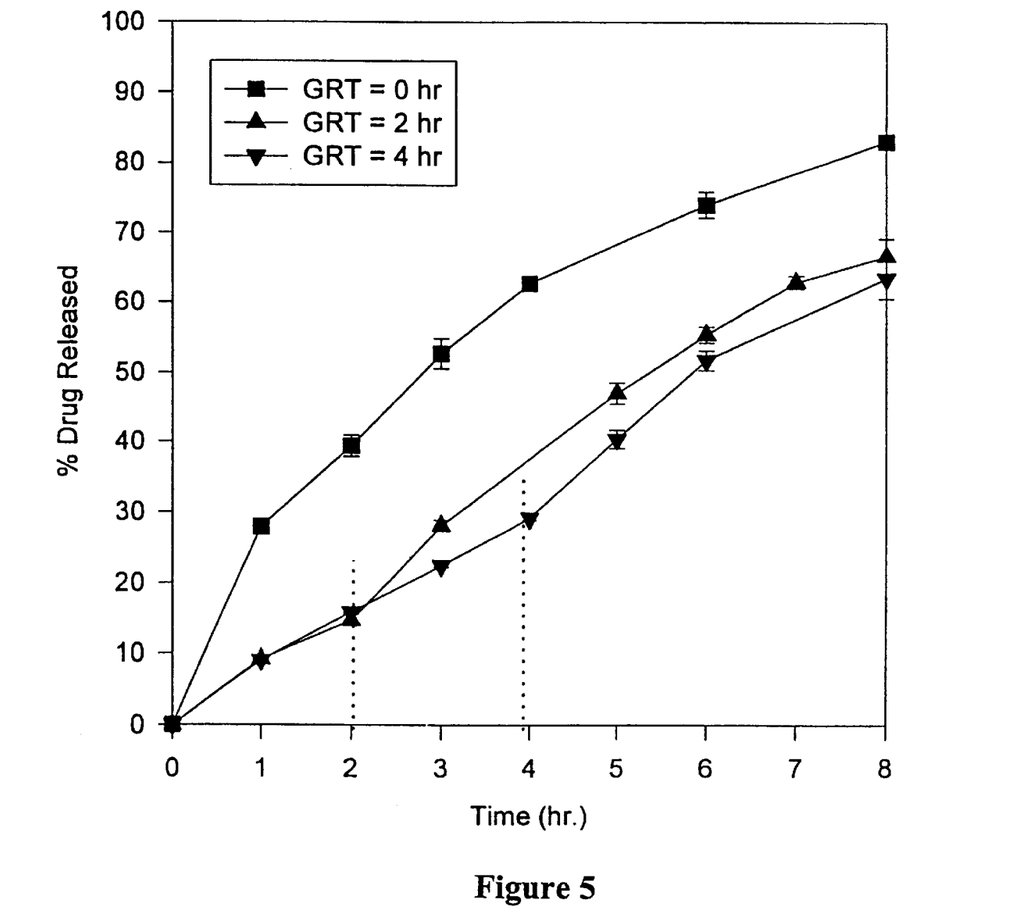
FIG. 5 is a graphical representation of data showing the effect of in vitro gastric residence time on the release of valproic acid from a prior art hydroxypropyl methylcellulose matrix formulation.
Figure 6:
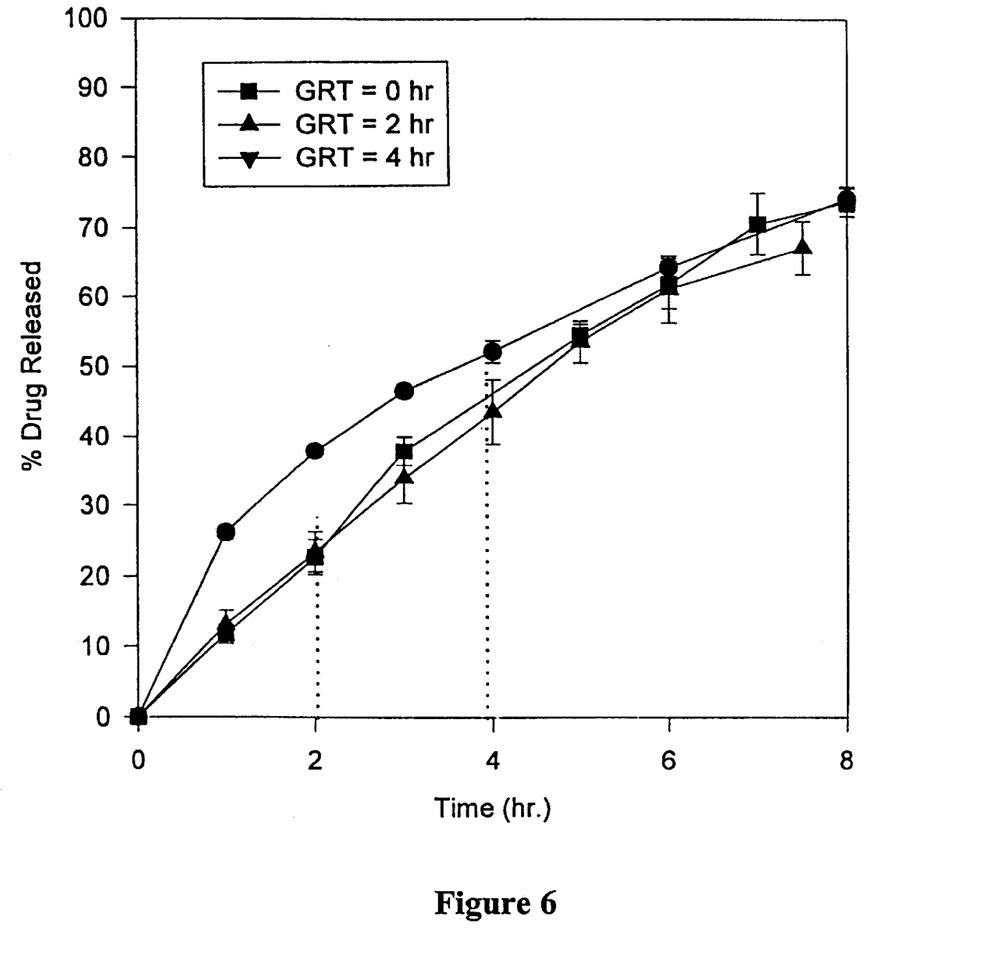
FIG. 6 is a graphical representation of data showing the effect of in vitro gastric residence time on the release of valproic acid from a formulation in accordance with the present invention.

In FIG. 5, the release rate from the prior art formulation shows a noticeable increase in the release rate (slope of the curve) upon change in pH (dotted lines at 2 hours and 4 hours) as would be expected when the acidic drug "moves" from the acidic environment of the stomach to the higher pH of the intestine where it is more soluble. In addition, with the prior art formulation of FIG. 5, there is a wider gap between the curves for the 2-hour and 4-hour gastric residence times. However, the data curves in FIG. 6 track one another much more closely where the drug is in a formulation of the present invention. The change in release rate after 2 hours gastric residence time is considerably less, and in the case of 4 hours gastric residence time is unnoticeable. These data indicate that the formulations of the present invention demonstrate reduced dependence of release upon gastric residence time in addition to their reduced dependence upon pH.

EXAMPLES

Formulation 1
Present Invention

Four-hundred-milligram tablets containing 60 mg of divalproex sodium, 140 mg of a copolymer of a dimethylaminoethyl-modified methacrylate and neutral methacrylates of weight average molecular weight about 150,000 Daltons ("Eudragit E-100," Röhm America), 100 mg of hydroxypropylmethyl cellulose (Methocel®, grade K4MP CR, Dow Chemical), and 100 mg of lactose. This formulation represented a drug loading of 15% by weight.

Bulk drug was milled prior to use. The milled bulk drug was dry-mixed with polymer and excipients. Tablets weighing 400 mg were pressed in a Model C Carver Press tableting machine using a round die (diameter=0.95 cm) at a compression force of about 2000 lbf (about $8.9 \times 10^3$ Newtons).

Formulation 2
Control Example

Tablets were prepared by the same method, and having the same composition, as described in Formulation 1 above, but lacking the dimethylaminomethyl-modified methacrylate polymer. The drug was dispersed in a hydroxypropylmethyl cellulose (HPMC) matrix.

Test Formulation 3
Comparative Example

Tablets were prepared by the same method, and having the same composition, as described above in Formulation 1, containing 140 mg of anhydrous dicalcium phosphate ("Fujicalin," Fuji Chemical Industries, Inc.) in place of the dimethylaminomethyl-modified methacrylate polymer.

Formulation 4
Comparative Example

Tablets were prepared by the same method, and having the same composition, as described above in Formulation 1, but containing 140 mg of magnesium aluminometasilicate ("Neusilin," Fuji Chemical Industries, Inc.) in place of the dimethylaminomethyl-modified methacrylate polymer.

In vitro dissolution tests in aqueous solutions at various pH values were conducted with each of the formulations described above using Apparatus II and the method detailed in the *United States Pharmacopeia XXI/National Formulary XVI*. The stirrer paddle speed of the apparatus was 100 rpm, and the temperature of the medium was maintained at 37° C. Dissolution of each of the formulations was observed and measured at two or more of three pH values: pH 1 (0.1 M HCl), pH 4.5 (0.05 M phosphate buffer), and pH 6.8 (0.05 M tribasic phosphate buffer).

Sample aliquots of 1.5 ml were withdrawn from the stirred samples at 0, 1, 2, 3, 4, 6 and 8 hours and filtered through a 0.45 μm filter. The aliquot samples were assayed for drug by fluorescent polarization immunoassay using the TDX® analyzer (Abbott Laboratories). Upon withdrawal of each sample, an equal volume of medium was added to the test mixture to maintain constant volume. The test results are shown in FIGS. 1–4.

Preferred Formulations of the Invention

Because of their superiority in controlling and regularizing the release of an acidic pharmacologic agent (e.g. divalproex sodium) over a wide pH range, compositions corresponding to Formulation 1 above comprising a neutral water-swellable polymer in combination with a polymer which is both soluble at acidic pH and water-swellable at neutral or alkaline pH, is the preferred formulation of the present invention. The formulation comprises a therapeutically effective amount of an acidic pharmacologic agent dissolved or dispersed in a polymer matrix comprising from about 10 weight percent to about 40 weight percent, preferably from about 15 weight percent to about 30 weight percent, of a pharmaceutically acceptable neutral, water-swellable, hydrophilic polymer in combination with from about 20 weight percent to about 50 weight percent, preferably from about 25 weight percent to about 40 weight percent of a pharmaceutically acceptable acid soluble polymer which is water swellable above pH 5, all percentages by weight based upon the total weight of the formulation. The balance of the formulation comprises pharmaceutically acceptable excipients such as diluents, binders, lubricants, glidants, disintegrating agents, and/or colorants and flavoring agents of the type generally known in the formulation arts and detailed further below.

Neutral, water-swellable, hydrophilic polymers suitable for use in the formulations of this invention include methylcellulose, hydroxymethylcellulose, hydroxyethylcellulose, hydroxypropylcellulose, carboxymethylcellulose, and hydroxypropyl methylcellulose and copolymers thereof. Neutral water-swellable modified cellulose polymers which may be used in the formulations of the present invention include, for example, Methocel®, grades E10MP CR, E4MP, K100V, K4MP, K15MP and K100MP (available from Dow Chemical); Klucel® HXF hydroxypropyl cellulose (available from Hercules, Inc.); Keltone®, grades LVCR and HVCR alginates (available from Kelco Co.). Polyox®, polyethylene oxide polymer (available from Union Carbide Co.), Keltrol®, xanthan gum (available from Kelco Co.), and Carbopol®, grades 934P, 971P, and 974P (available from B.F. Goodrich Specialty Chemicals). A preferred neutral, water-swellable polymer for formulations of the present invention is Methocel® K4MP, a cellulose ether comprising about 19–24% methoxyl substitution and about 7–12% hydroxypropyl substitution having a 2% aqueous nominal viscosity of about 4000 centipoise (4 pascal-seconds).

Polymers suitable for use in formulations of the present invention which are acid-soluble and which swell in water at higher values of pH, are methacrylic acid/methacrylic ester copolymers which have been modified by the incorporation of a basic functional group such as an amino-, alkylamino-, dialkylamino-, or dialkylaminoalkyl-group. These materials are soluble at acidic pH values because of protonation at the sites of basic nitrogen atoms contained within the polymer to form ionized ammonium groups. These materials are also thus designated as "acid ionizable" or "salt-forming" methacrylic acid/methacrylic ester copolymers. Acid-soluble modified methacrylate polymers which swell in water at neutral or alkaline pH values which may be used in formulations of the present invention include Eudragit® E100 which is a cationic copolymer based on dimethylaminoethyl methacrylate and neutral methacrylates, having a molecular weight of about 150,000 Daltons, (available from Röhm America, Inc.).

Excipients

In addition to the active pharmacologic agent and polymer matrix, pre-compressed or compressed formulations of the present invention may contain additives or excipients which act in one or more capacities as diluents, binders, lubricants, glidants, disintegrating agents, colorants or flavoring agents.

In those situations where the amount of active pharmacologic agent in a tablet is small, one or more inert diluents is added to increase the bulk of the tablet. Diluents used for this purpose include dicalcium phosphate, calcium sulfate, dextrose, amylose lactose, microcrystalline cellulose, kaolin, mannitol, sodium chloride, dry starch and powdered sugar.

Binders impart cohesiveness to the tablet formulation, insuring that the tablet remains intact after compression, as well as improving the free-flowing characteristics and desired hardness of pre-tabletting granulations. Materials commonly used as binders include starch, gelatin, and sugars such as sucrose, glucose, dextrose, molasses and lactose. Natural and synthetic gums such as acacia, sodium alginate, extract of Irish moss, panwar gum, ghatti gum, carboxymethylcellulose, methyl cellulose, and polyvinylpyrrolidone may also be used as binders.

Lubricants serve a number of functions in tablet formulation including the prevention of adhesion of the pressed tablet to the surface of dies and punches, facilitation of release of the tablet from the die, and improving the flow rate of pre-tabletting granulations. Commonly used lubricants include talc, magnesium stearate, calcium stearate, stearic acid, hydrogenated vegetable oils and poly(ethylene glycol). The quantity of lubricant used in the tablet formulation may varying between a low of about 0.1 weight percent to as high as about 5 weight percent.

Glidants improve the flow characteristics of dry powdered mixtures. Colloidal silicon dioxide is most commonly used as a glidant, although asbestos-free talc is also sometimes used. The glidant, when used, typically constitutes about 1 weight percent or less of the formulation.

Disintegrating agents, either as single substances or as mixtures, are added to tablet formulations to facilitate the break-up or disintegration of the tablet after administration. Corn and potato starch, which have been well dried and powdered, are the most commonly used tablet disintegrating agents. The amount of starch added to the formulation varies, depending upon the rate of disintegration desired, and ranges between about 5 weight percent and about 10 to 15 weight percent. Swelling disintegrating agents such as croscarmelose, crospovidone, and sodium starch glycolate represent, respectively, examples of cross-linked cellulose, cross-linked polymer, and cross-linked starch agents which may also be used. These materials are typically used in amounts ranging between about 2 and 4 weight percent in the tablet formulation.

Coloring agents may be added to the tablet formulation or to a polymeric material used as a tablet coating. Suitable coloring agents include those approved for use by the United States Food and Drug Administration (FDA) and are well known to those of the formulation arts.

Tabletting Processes

Tablets are generally prepared by one of three methods well known to those skilled in the art: wet granulation, dry granulation, or direct compression. Any of the three methods may be used to formulate tablets in accordance with the present invention.

While there have been shown and described what are believed to be the preferred embodiments of the present invention, it will be apparent to those of ordinary skill in the pharmaceutical formulating art that various modifications in the formulations and processes herein described can be made without departing from the scope of the invention as it is defined by the appended claims.

We claim:

1. A pharmaceutical composition comprising a therapeutically effective amount of an acidic pharmacologic agent dissolved or dispersed in a polymer matrix comprising a) from about 10 weight percent to about 40 weight percent of a pharmaceutically acceptable neutral, water-swellable, hydrophilic polymer, and b) from about 15 weight percent to about 50 weight percent of a pharmaceutically acceptable acid soluble polymer which is water swellable above about pH 5, all percentages based upon the total weight of the formulation.

2. The pharmaceutical composition according to claim 1 wherein said polymer matrix comprises from about 20 weight percent to about 30 weight percent of said pharmaceutically acceptable neutral, water-swellable, hydrophilic polymer.

3. The pharmaceutical composition according to claim 1 wherein said polymer matrix comprises from about 20 weight percent to about 40 weight percent of said pharmaceutically acceptable acid-soluble polymer which is water swellable above about pH 5.

4. The pharmaceutical composition of claim 1 wherein said neutral, water-swellable, hydrophilic polymer comprises a polymer selected from the group consisting of methylcellulose, hydroxymethylcellulose, hydroxyethylcellulose, hydroxypropylcellulose, carboxymethylcellulose, hydroxypropyl methylcellulose and copolymers thereof, poly(ethylene oxide) polymer, cross-linked homopolymers and copolymers of acrylic acid, xanthum gum, and alginate.

5. The pharmaceutical composition of claim 1 wherein said acid-soluble polymer which is water-swellable above about pH 5 comprises a methacrylate polymer modified with a basic functional group.

6. The pharmaceutical composition of claim 5 wherein said acid-soluble polymer which is water-swellable above about pH 5 comprises a dialkylaminoalkyl-modified methacrylate polymer.

7. A pharmaceutical composition comprising a therapeutically effective amount of an acidic pharmacologic agent dissolved or dispersed in a matrix comprising from about from about 10 weight percent to about 40 weight percent of a pharmaceutically acceptable neutral water-swellable cellulosic polymer and from about 15 weight percent to about 50 weight percent of an acid-soluble polymer comprising a dialkylaminoalkyl-modified methacrylate polymer which is water swellable above about pH 5, all percentages based upon the total weight of the composition.

8. The composition of claim 7 wherein said acidic pharmacologic agent is a compound having a pKa value below about 6.

9. The pharmaceutical composition of claim 8 wherein said pharmaceutically acceptable neutral water-swellable cellulosic polymer is present in an amount ranging between about 20 weight percent and about 30 weight percent, based on the total weight of the composition.

10. The pharmaceutical composition of claim 8 wherein said pharmaceutically acceptable acid-soluble polymer which is water swellable above pH 5 is present in an amount ranging between about 20 weight percent and about 40 weight percent, based on the total weight of the composition.

11. The pharmaceutical composition of claims 8, 9 or 10 wherein the acidic pharmacologic agent is divalproex sodium.

12. A pharmaceutical composition comprising a therapeutically effective amount of an acidic pharmacologic agent dissolved or dispersed in a matrix comprising from about 10 weight percent to about 40 weight percent of a neutral water-swellable cellulosic polymer and from about 15 weight percent to about 50 weight percent of an acid-soluble dialkylaminoalkyl-modified methacrylate polymer which swells in water above about pH 5, all weight percentages based upon the total weight of the composition.

13. The pharmaceutical composition of claim 12 wherein said neutral, water-swellable, hydrophilic polymer comprises a polymer selected from the group consisting of methylcellulose, hydroxymethylcellulose, hydroxyethylcellulose, hydroxypropylcellulose, carboxymethylcellulose, and hydroxypropyl methylcellulose and copolymers thereof.

14. The pharmaceutical composition of claim 12 wherein said acid-soluble dialkylaminoalkyl-modified methacrylate polymer is a dimethylaminoethyl-modified methacrylate polymer.

15. The pharmaceutical composition of claim 12 wherein said acidic pharmacologic agent is divalproex sodium.

16. A pharmaceutical dosage form comprising a therapeutically effective amount of divalproex sodium dissolved or dispersed in a matrix comprising from about 10 weight percent to about 40 weight percent of a neutral water-swellable cellulosic polymer and from about 20 weight percent to about 50 weight percent of an acid-soluble dialkylaminoalkyl-modified methacrylate polymer which is water swellable at pH values above 5, all percentages based upon the total weight of the dosage form.

17. A dry granular composition suitable for compressing into a tablet dosage form, comprising particles containing an acidic pharmacologic agent dissolved or dispersed in a matrix comprising from about 10 weight percent to about 40 weight percent of a neutral, water swellable hydrophilic polymer and from about 20 weight percent to about 50 weight percent of an acid soluble polymer which is water swellable at pH values above about 5, all weight percentages based upon the total weight of the granular composition.

18. The granular composition of claim 17 wherein said matrix comprises from about 20 weight percent to about 30 weight percent of said neutral water-swellable hydrophilic polymer.

19. The granular composition of claim 17 wherein said matrix comprises from about 20 weight percent to about 40 weight percent of said acid soluble polymer which is water swellable at pH values above 5.

20. The granular composition of claim 17 wherein said acidic pharmacologic agent is divalproex sodium.

21. The granular composition of claim 17 wherein said neutral water-swellable hydrophilic polymer is selected from the group consisting of methylcellulose, hydroxymethylcellulose, hydroxyethylcellulose, hydroxypropylcellulose, carboxymethylcellulose, and hydroxypropyl methylcellulose and copolymers thereof.

22. The granular composition of claim 17 wherein said acid-soluble polymer which is water-swellable at pH values above about 5 comprises a dialkylaminoalkyl-modified methacrylate polymer.

23. A process for preparing a granular pharmaceutical composition suitable for pressing into tablets comprising the steps of
   a) dry blending a mixture of from about 5 weight percent to about 50 weight percent of an acidic pharmacologic agent, from about 20 weight percent to about 40 weight percent of a neutral, water-swellable hydrophilic polymer, and from about 20 weight percent to about 50 weight percent of an acid soluble polymer which is water-swellable at pH values above about 5 to form a uniform mixture;
   b) wet granulating the dry uniform mixture from step a); and
   c) drying and sizing the wet granules from step b),
wherein all percentages are based upon to total weight of the granulation.

24. The process of claim 23 wherein said neutral, water-swellable hydrophilic polymer comprises hydroxypropyl methyl cellulose.

25. The process of claim 23 wherein said acid-soluble polymer which is water swellable at pH values above about 5 is a dialkylaminoalkyl-modified methacrylate polymer.

26. A process according to claim 23 wherein said acidic pharmacologic agent is divalproex sodium.

27. A method of preparing a controlled release tablet dosage form of an acidic pharmacologic agent comprising the steps of
   a) dry blending a mixture of from about 5 weight percent to about 50 weight percent of an acidic therapeutic agent, from about 20 weight percent to about 40 weight percent of a neutral, water-swellable hydrophilic polymer, from about 20 weight percent to about 50 weight percent of an acid soluble polymer which is water-swellable at pH values above about 5 to form a uniform mixture;
   b) wet granulating the dry uniform mixture from step a);
   c) drying and sizing the wet granules from step b); and
   d) compressing the blended granules of step c) under a force ranging between about 2000 lbf (about $8.9 \times 10^3$ Newtons) and about 10,000 lbf (about $4.45 \times 10^4$ Newtons).

28. The process of claim 27 wherein said neutral, water-swellable hydrophilic polymer comprises hydroxypropyl methyl cellulose.

29. The process of claim 27 wherein said acid-soluble polymer which is water swellable at pH values above about 5 is a dialkylaminoalkyl-modified methacrylate polymer.

30. A process according to claim 27 wherein said acidic pharmacologic agent is divalproex sodium.

* * * * *